United States Patent [19]

Anderson et al.

[11] 4,154,111
[45] May 15, 1979

[54] COTTON DUST ANALYZER

[75] Inventors: Joe D. Anderson; Roy V. Baker, both of Lubbock, Tex.

[73] Assignee: The United States of America as represented by the Secretary of Agriculture, Washington, D.C.

[21] Appl. No.: 893,367

[22] Filed: Apr. 4, 1978

[51] Int. Cl.² .................... G01N 13/02; B01D 35/24
[52] U.S. Cl. ..................... 73/432 PS; 55/97; 55/270
[58] Field of Search ........ 73/432 PS, 421 R, 421.5 R; 55/96, 97, 270

[56] References Cited

U.S. PATENT DOCUMENTS

| | | | |
|---|---|---|---|
| 1,704,418 | 3/1929 | Abbott | 73/421 R |
| 2,237,417 | 4/1941 | Croft | 55/96 |
| 2,509,264 | 5/1950 | Cox | 73/422 R |
| 3,309,518 | 3/1967 | Weiss | 73/421 R |
| 3,572,128 | 3/1971 | Hemeon | 73/421 R |
| 3,608,379 | 9/1971 | Brevko et al. | 73/432 PS |
| 3,748,905 | 7/1973 | Fletcher et al. | 73/421.5 R |

Primary Examiner—Daniel M. Yasich
Attorney, Agent, or Firm—M. Howard Silverstein; Salvador J. Cangemi; David G. McConnell

[57] ABSTRACT

An apparatus for sampling dust from lint cotton is disclosed. Air is blown through a known sample of lint cotton positioned in a holding fixture to remove the dust. A suction means is provided to move and direct the dust removed from the lint cotton sample to a filtering means which gathers the dust for subsequent weighing. This accurate dust sample is then used to program experiments for improving the health and safety conditions in the lint cotton process as well as the efficiency of the machinery used in lint cotton processing.

4 Claims, 4 Drawing Figures

COTTON DUST ANALYZER

BACKGROUND OF THE INVENTION

1. FIELD OF THE INVENTION

This invention relates to the sampling of dust in lint cotton.

2. DESCRIPTION OF PRIOR ART

The presence of cotton dust in lint has long been a problem in the processing of lint cotton, since some of the dust escapes into the atmosphere during processing. This atmospheric dust creates health hazards to the workers as well as fouling machinery and cutting down on the efficiency of the operation.

At present research dealing with worker respiratory problems are conducted in model card rooms. This requires a large volume of lint processing through the machinery of a model card room so that the dust concentrations in the room air may be measured. In other instances animal or human subjects are used to detect the presence of a causative agent for respiratory problem.

There is also a limiting factor from dust accumulating in the turbines in the open end spinnning process. This has resulted in the spinning of large volumes of lint in order to determine the effects of experimental treatments.

SUMMARY AND OBJECTS OF THE INVENTION

The instant invention serves as a significant improvement in the art in that it provides a rapid, accurate and inexpensive determination of the dust generation potential of lint cotton and in many cases eliminate the need for model card room testing and gives an accurate inexpensive determination of dust in the lint cotton. A lint cotton sample is placed in a holding device. Dust contained in the lint cotton is blown from the sample and gathered on a preweighed filter. A suction means is utilized in moving and directing the dust laden air onto said filter. The filter containing the dust is then again weighted and the amount of dust in the lint cotton sample determined accurately, since an enclosure around the apparatus eliminates any atmospheric dust interference as well as producing efficient air flow through the apparatus. This dust sample can then be used in health, safety and machinery efficiency studies.

It is the primary object of the invention to accurately measure the amount of dust in lint cotton.

It is another object of the invention to eliminate bulky expensive card modeling rooms with a small inexpensive accurate means of measuring dust in cotton.

It is another object of the invention to use the dust measurements for improving health and safety conditions in the lint cotton processing industry.

It is another object of the invention to use the dust measurements for improving the efficiency of the machinery used in lint cotton processing.

Other objects of the invention will become obvious from the detailed description of the preferred embodiments of the invention.

DESCRIPTION OF THE PREFERRED EMBODIMENTS

Figure 1:
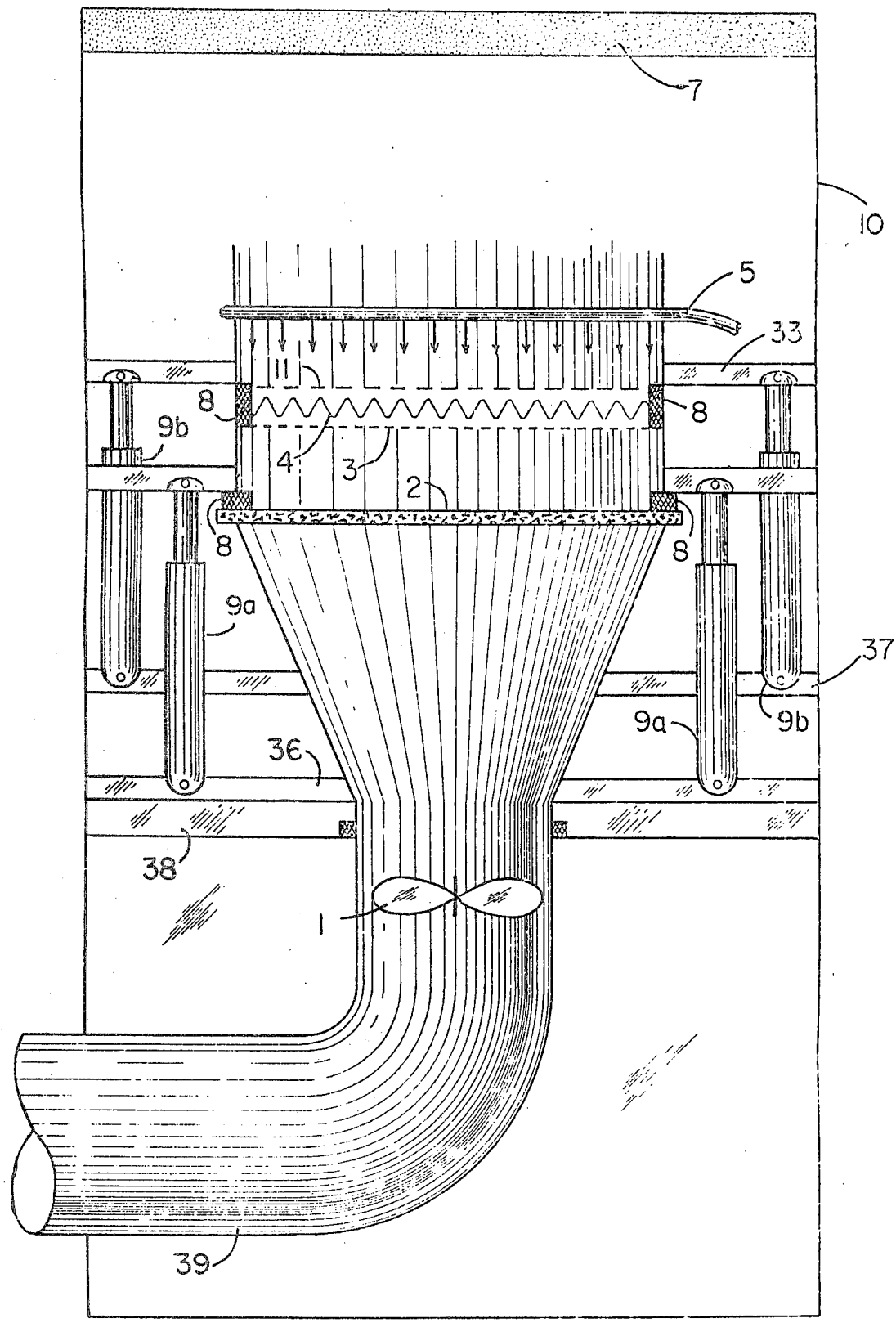
FIG. 1 is a partial cross-section of the entire fine dust analyzer.

Referring now to FIG. 1 wherein a specimen of cotton lint 4 is placed between two screens 3 and 11 which form a sample holding means. Compressed air from spray bar 5 is blown through lint specimen 4 to release fine dust which is entrapped in lint specimen 4. Spray bar 5 is located adjacent and parallel to screens 3 and 11.

The compressed air is filtered (not shown) and freed from moisture by an inline filter and water trap before it reaches spray bar 5. Compressed air pressure at the spray bar is maintained at 24 psi but may range between 20 and 35 psi. The sample holding means, mounted in enclosure 10, comprises top holding screen 11 in parallel with bottom holding screen 3. Sample 4 is held in between top holding screen 11 and bottom holding screen which is sized to allow specific dust sized particles to pass through when air is blown through the sample. Mesh of screen 3 can be selected to size out any size particle desired. One hundred sixty-five mesh allowing 100 micron or less particle size to pass through was used in the instant invention. However, any size may be used. Top screen 11 is mainly to keep lint specimen 4 in place and not be blown out of position as spray bar 5 blows the compressed air through lint specimen 4. A 25 mesh screen was used for this application although any size screen is acceptable as long as it efficiently holds the sample in.

Figure 2:
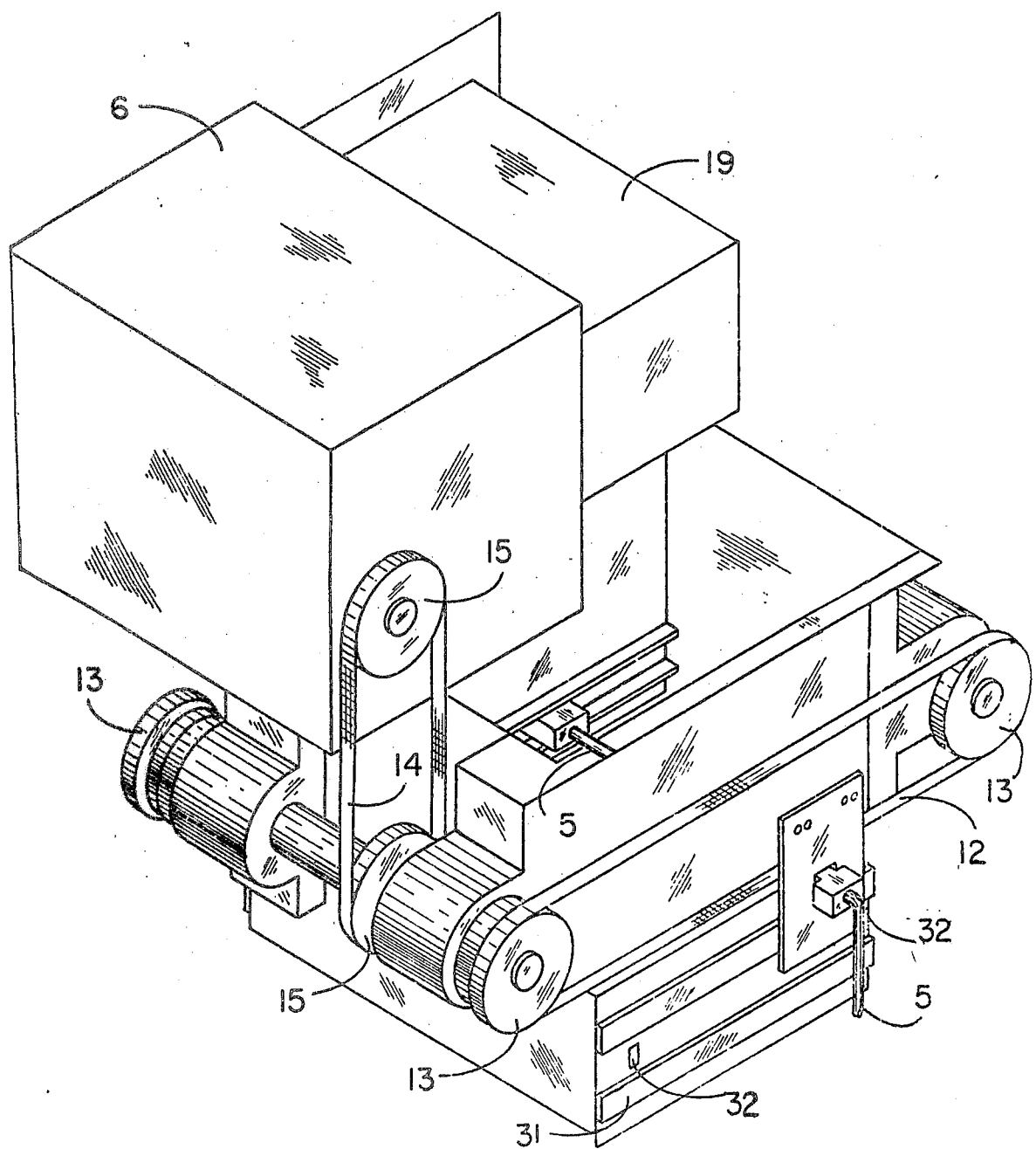
FIG. 2 is a view of the spray bar and drive assembly.
Figure 3:
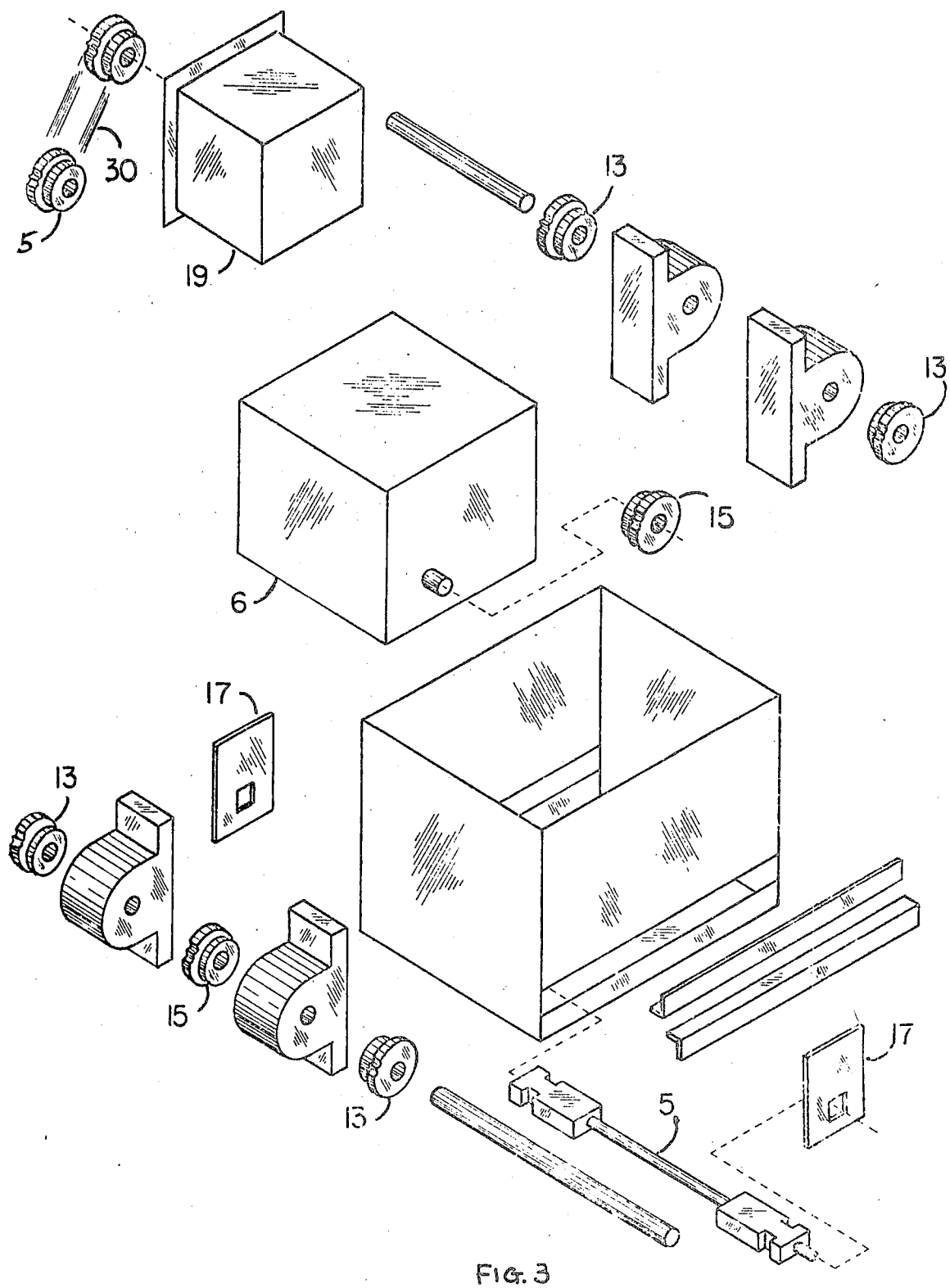
FIG. 3 is an exploded view of the spray bar and drive assembly.
Figure 4:
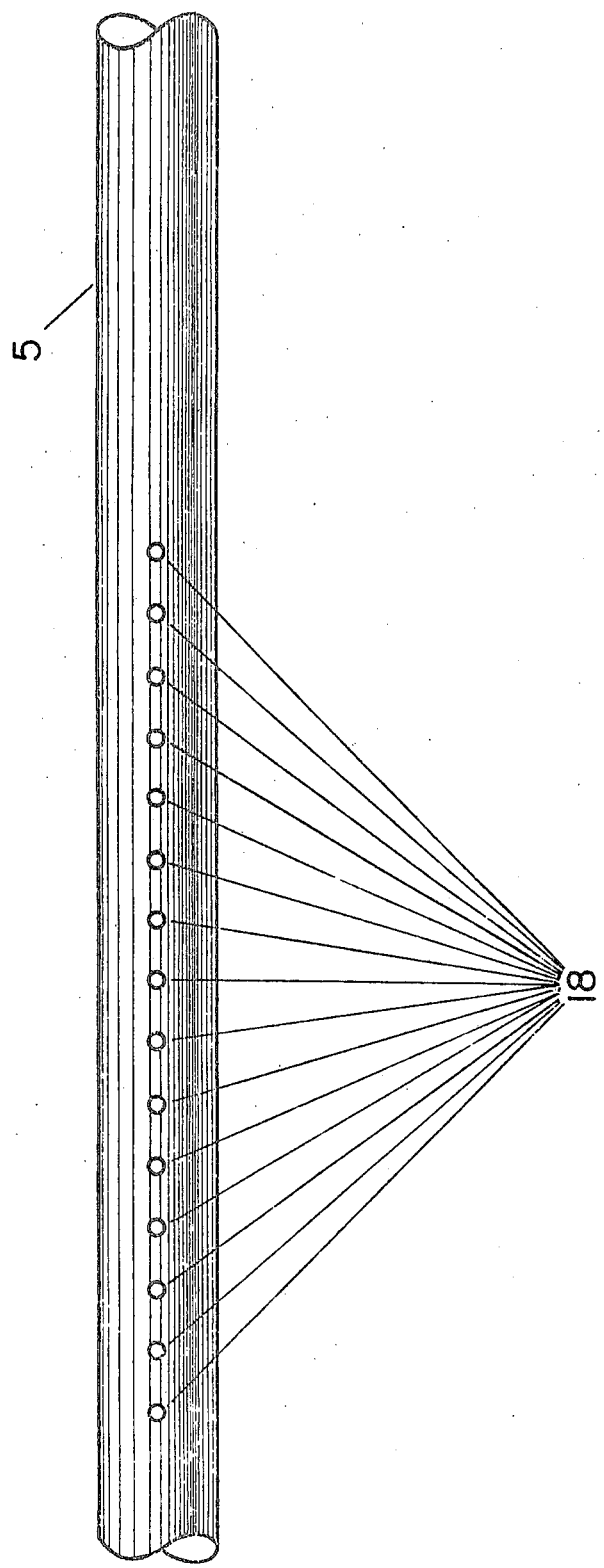
FIG. 4 is a bottom view of the spray bar.

Spray bar 5 is a ½-inch diameter stainless steel tube or pipe with fourteen 1/16-inch diameter holes 18 drilled ⅜ inches apart (FIG. 4) in a straight line on the surface of the tube. The spray bar 5 is located parallel and 1¼ inches from the sample holding means. However, the material does not matter and any metal or plastic may be substituted. However, the number of holes, size of holes, and spacing is critical. Improperly sized holes do not produce enough velocity and improper spacing results in low volumes and velocities of air through the sample especially if the holes are too large or too far apart. Spray bar 5 (FIGS. 1 and 2) is located 1-¼ inches above screen 11. This distance was arrived at after much experimentation and is a very critical distance. If spray bar 5 is too far away from sample 4 the air velocity will drop too low. If it is too close, it will result in too high a concentration of air in one spot and improper sample cleaning. Even though hole size, hose spacing and spray bar location were very critical in the instant invention, it may be possible after extensive experimentation to find other combinations of these factors that would be equally effective. In the operation of the instant invention, spray bar 5 is moved back and forth blowing air through lint specimen 4 and assuring adequate dust removal across the entire specimen. The back and forth operation is automatic and set on a timer (not shown). Spray bar 5 is connected to a π25 roller chain 12 (FIG. 2) by a ⅛-inch steel plate 17 so that spray bar 5 can be moved easily back and forth above lint specimen 4 by roller chain 12 of a first chain drive. The first chain drive consists of a #25 roller chain 12 and a #25 20-toothed sprocket 13 and is connected to an anti-backlash reversing drive 6 by a second chain drive which is a #25 roller chain 14 and #25 20-tooth sprocket 15. Reversing drive 6 is used to drive chain drive 12 and 13 backward and forward so that spray bar 5 can be pulled back and forth above lint specimen 4. Reversing drive 6 and gear motor 19 are connected by a third chain drive #25 roller chain 30 and a third set of #25 20-tooth sprockets 16 (FIG. 3). Thus spray bar 5 (FIG. 2) is driven between guiding angle bars or rails 31 back and forth. Guide rails 31 are comprised of a set of two parallel rails 31. Reverse action is initiated by a set of micro switches 32 at each end of angle bars or rails 31 to accomplish reversing direction. There is an identical set of guiding angle bars or rails (not shown) on the other side of the machine. Micro switches 32 accomplish reversing direction by controlling reversing drive 6 which is the driving means.

After the compressed air from spray bar (FIG. 1) passes through lint specimen 4 blowing the fine dust through bottom screen 3 the air and dust are pulled to a Gelman Type A/E Fiberglass Filter 2 which forms a filtering means by a suction created by a high volume air sampler motor and fan 1. Filter 2 catches the fine dust while air passes on through. Filter 2 is located adjacent and parallel to the sample holding means and on the opposite side of the sample holding means from spray bar 5. The air and dust are prevented from escaping until they have been filtered by filter 2. This seal is formed by the use of foam rubber weather-stripping 8 which forms a seal around the edges of filter 2 and lint specimen 4.

The entire mechanism is enclosed by a sheet metal enclosure 10 so that the air needed by the air sampler motor and fan 1 which is not provided by the compressed air from spray bar 5 will be filtered through a ¾-inch thick foam rubber sheet 7 on the top or upstream side of enclosure 10 as air is sucked through thus insuring that all air is free of any atmospheric dust. The enclosure has an exhaust opening 40 at the downstream end of the apparatus.

When changing filter 2 and lint specimen 4, enclosure 10 is raised and lowered by a set of standard double acting air cylinders 9a and 9b which are set in the vertical position on each side of the filter 2 and sample holding means, said air cylinders provided to raise and lower the top part of said envelope. Vertical air cylinders 9a and 9b are mounted to permanent mounting supports 35 and 36. These air cylinders are necessary due to the large size and weight of the sampler. Cylinders 9a and 9b are activated and enclosure 10 separates at intersection or 33 forming a top and bottom half. Interface 33 is located at the approximate location of the sample holding means and opens approximately 6" to 8" which is enough to change the filter and specimen. Cylinders 9a rest on support members 36 and cylinders 9b rest on support members 35. Fan 1 rests on support member 38. After changing filter and specimen cylinders 9a and 9b are lowered and enclosure 10 resealed.

The instant invention a 3-⅓ gram lint specimen was used. These specimens are approximately 7×8-inches in size and ¼ inch thick.

Filter 2 and lint specimen 4 are weight prior to cycling the blown air through them and weighed again after sampling so that the amount of dust dislodged from the lint specimen 4 could be determined by the change in filter 2 weight.

The instant invention may be constructed from any material capable of furnishing the sufficient rigidity for support of the sampler and the air blowing machinery.

We claim:
1. An apparatus for extracting cotton dust for the purpose of determining dust generation potential of a lint cotton specimen comprising in combination:
   (a) a sample holding means containing a lint cotton sample which is impregnated with dust;
   (b) a means of blowing air through said lint cotton sample and removing the dust from said lint cotton, said air blowing means located adjacent and parallel to said sample holding means;
   (c) a filtering means to capture said dust removed from said sample, said filtering means located adjacent and parallel to said sample holding means and on the opposing side of said sample holding means from said air blowing means;
   (d) a suction means to move the dust laden air which is blown from the lint cotton sample and direct said dust to said filtering means where said dust is captured by a filter of said filtering means;
   (e) an enclosure around the above to enclosed said apparatus from the atmosphere and provide for air flow through said apparatus, said enclosure comprising:
      (1) a filtered opening at the upstream end allowing for air suction; and,
      (2) an exhaust opening at the down stream end of the apparatus;
   (f) a means of changing said sample and said filter comprising:
      (1) an interface where said enclosure separates into two parts, said interface located at the approximate location of said sample holding means;
      (2) a set of double acting air cylinders mounted on said enclosure in a vertical position on each side of said filter and said sample holding means, said air cylinders being parallel and adjacent to said filter and said sample holding means, said air cylinders provided to raise and lower the top part of said enclosure.

2. The apparatus of claim 1 wherein the sample holding means comprises in combination a top holding screen in parallel with a bottom holding screen, said sample held in-between and said bottom holding screen sized to allow specific dust sized particles to pass through when air is blown through said sample.

3. The apparatus of claim 1 including a means of automatically moving the air blowing means back and forth comprising in combination:
   (a) a first chain drive affixed to said air blowing means;
   (b) a second chain drive communicating with said first chain drive;
   (c) an anti-backlash reversing drive, driving said second chain drive backward and forward.
   (d) a third chain drive connecting said reversing drive and a gear motor;
   (e) a set of parallel guide rails to guide said air blowing means backward and forward;
   (f) a set of micro switches to reverse the motion on said air blowing means.

4. The apparatus of claim 1 wherein the top part of the enclosure is raised and lowered approximately 6 to 8 inches for top and bottom enclosure separation.

* * * * *